US012178739B2

(12) United States Patent
Hansen et al.

(10) Patent No.: US 12,178,739 B2
(45) Date of Patent: Dec. 31, 2024

(54) OSTOMY APPLIANCE HAVING AN ELECTRICAL CONNECTOR

(71) Applicant: Coloplast A/S, Humlebaek (DK)

(72) Inventors: Jais Ask Hansen, Jaegerspris (DK); Lars Erup Larsen, Maaloev (DK); Niels Hvid, Vedbaek (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 18/121,013

(22) Filed: Mar. 14, 2023

(65) Prior Publication Data

US 2023/0293335 A1 Sep. 21, 2023

Related U.S. Application Data

(63) Continuation of application No. 16/954,524, filed as application No. PCT/DK2018/050398 on Dec. 20, 2018, now Pat. No. 11,628,084.

(30) Foreign Application Priority Data

Dec. 22, 2017 (DK) ........................... PA 2017 70999

(51) Int. Cl.
*A61F 5/443* (2006.01)
*A61B 5/00* (2006.01)
*A61F 5/445* (2006.01)

(52) U.S. Cl.
CPC ............ *A61F 5/443* (2013.01); *A61B 5/0002* (2013.01); *A61B 5/4851* (2013.01); *A61B 5/6833* (2013.01); *A61F 5/445* (2013.01)

(58) Field of Classification Search
CPC . A61F 5/443; A61F 5/445; A61F 5/44; A61B 5/0002; A61B 5/4851; A61B 5/6833
See application file for complete search history.

(56) References Cited

U.S. PATENT DOCUMENTS 2,054,535 A 9/1936 Diack
2,327,514 A 8/1943 Fenwick
(Continued)

FOREIGN PATENT DOCUMENTS

CA 2202199 C 8/2006
CN 203786580 U 8/2014
(Continued)

OTHER PUBLICATIONS

International Preliminary Report on Patentability received for PCT Patent Application No. PCT/DK2019/050243, mailed on Feb. 25, 2021, 12 pages.

(Continued)

*Primary Examiner* — Amanda K Hulbert
*Assistant Examiner* — Natasha Patel
(74) *Attorney, Agent, or Firm* — Coloplast Corp., Coloplast A/S; Nick Baumann

(57) ABSTRACT

A monitor device and a base plate and an ostomy system comprising a monitor device and a base plate is disclosed. The base plate comprising: a top layer; an electrode assembly; and a monitor interface configured for connecting the base plate to a monitor device. An axial distance along an axial direction between a proximal facing edge of a coupling part and a contact surface on the distal side of the top layer is a first axial distance. The first axial distance being less than a second axial distance between a distal facing edge of the monitor device and a proximal facing side of the monitor device, such that upon connecting the base plate to the monitor device the proximal facing side of the monitor device contacts the contact surface to force a first connection parts to contact a first terminal element.

11 Claims, 12 Drawing Sheets

(56) References Cited

U.S. PATENT DOCUMENTS

| | | |
|---|---|---|
| 2,542,233 A | 2/1951 | Carroll |
| 2,544,579 A | 3/1951 | Ardner |
| 3,214,502 A | 10/1965 | Schaar |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,167,650 A | 12/1992 | Johnsen et al. |
| 5,197,895 A | 3/1993 | Stupecky |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,570,082 A | 10/1996 | Mahgerefteh et al. |
| 5,593,397 A | 1/1997 | La Gro |
| 5,626,135 A | 5/1997 | Sanfilippo |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries et al. |
| 5,834,009 A | 11/1998 | Sawers et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,057,689 A | 5/2000 | Saadat |
| 6,103,033 A | 8/2000 | Say et al. |
| 6,135,986 A | 10/2000 | Leisner et al. |
| 6,165,005 A | 12/2000 | Mills et al. |
| 6,206,864 B1 | 3/2001 | Kavanagh et al. |
| 6,246,330 B1 | 6/2001 | Nielsen |
| 6,297,422 B1 | 10/2001 | Hansen et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | Von et al. |
| 6,520,943 B1 | 2/2003 | Wagner |
| 6,659,989 B1 | 12/2003 | Otto |
| 6,677,859 B1 | 1/2004 | Bensen |
| 6,764,474 B2 | 7/2004 | Nielsen et al. |
| 7,049,478 B1 | 5/2006 | Smith |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,221,279 B2 | 5/2007 | Nielsen |
| 7,326,190 B2 | 2/2008 | Botten |
| 7,341,578 B2 | 3/2008 | Bulow et al. |
| 7,347,844 B2 | 3/2008 | Cline et al. |
| 7,367,965 B2 | 5/2008 | Poulsen et al. |
| 7,422,578 B2 | 9/2008 | Shan et al. |
| 7,559,922 B2 | 7/2009 | Botten |
| 7,625,362 B2 | 12/2009 | Boehringer et al. |
| 7,641,612 B1 | 1/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,398,575 B1 | 3/2013 | Mccall |
| 8,398,603 B2 | 3/2013 | Thirstrup et al. |
| 8,399,732 B2 | 3/2013 | Oelund et al. |
| 8,409,158 B2 | 4/2013 | Edvardsen et al. |
| 8,449,471 B2 | 5/2013 | Tran |
| 8,474,338 B2 | 7/2013 | Gelman et al. |
| 8,500,718 B2 | 8/2013 | Locke et al. |
| 8,632,492 B2 | 1/2014 | Delegge |
| 8,680,991 B2 | 3/2014 | Tran |
| 8,684,982 B2 | 4/2014 | Nguyen-Demary et al. |
| 8,740,865 B2 | 6/2014 | Krystek et al. |
| 8,795,257 B2 | 8/2014 | Coulthard et al. |
| D712,545 S | 9/2014 | Igwebuike et al. |
| 8,821,463 B2 * | 9/2014 | Grum-Schwensen ............ A61F 5/443 604/332 |
| 8,821,464 B2 | 9/2014 | Hanuka et al. |
| 8,975,465 B2 | 3/2015 | Hong et al. |
| 8,979,813 B2 | 3/2015 | Uveborn |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,629,779 B2 | 4/2017 | Grum-Schwensen et al. |
| 9,629,964 B2 | 4/2017 | Wuepper |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,406,525 B2 | 8/2022 | Seres et al. |
| 11,471,318 B2 | 10/2022 | Hansen et al. |
| 11,491,042 B2 | 11/2022 | Seres et al. |
| 11,534,323 B2 | 12/2022 | Hansen et al. |
| 11,540,937 B2 | 1/2023 | Hansen et al. |
| 11,547,595 B2 | 1/2023 | Hansen et al. |
| 11,547,596 B2 | 1/2023 | Hansen et al. |
| 11,559,423 B2 | 1/2023 | Speiermann et al. |
| 11,559,426 B2 | 1/2023 | Sletten et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0068244 A1 | 4/2004 | Salone et al. |
| 2004/0078219 A1 | 4/2004 | Kaylor et al. |
| 2004/0100376 A1 | 5/2004 | Lye et al. |
| 2004/0106908 A1 | 6/2004 | Leise et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |

(56) References Cited

U.S. PATENT DOCUMENTS

| | | |
|---|---|---|
| 2006/0194324 A1 | 8/2006 | Faries et al. |
| 2006/0271002 A1 | 11/2006 | Botten |
| 2007/0010256 A1 | 1/2007 | Klabunde et al. |
| 2007/0035405 A1 | 2/2007 | Wada et al. |
| 2007/0135782 A1 | 6/2007 | Bager et al. |
| 2007/0142796 A1 | 6/2007 | Mosbacher et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0096726 A1 | 4/2008 | Riley et al. |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0009342 A1 | 1/2009 | Karjalainen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0216169 A1 | 8/2009 | Hansen et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1 | 2/2010 | Thirstrup et al. |
| 2010/0036206 A1 | 2/2010 | Lorio |
| 2010/0072271 A1 | 3/2010 | Thorstensson |
| 2010/0076275 A1 | 3/2010 | Chu et al. |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2011/0144470 A1* | 6/2011 | Mazar .................. A61B 5/257 600/391 |
| 2011/0191044 A1* | 8/2011 | Stafford ................ C12Q 1/006 702/65 |
| 2012/0013130 A1 | 1/2012 | Jung |
| 2012/0089037 A1* | 4/2012 | Bishay .................. A61B 5/335 600/509 |
| 2012/0143154 A1 | 6/2012 | Edvardsen et al. |
| 2012/0143155 A1 | 6/2012 | Edvardsen et al. |
| 2012/0172673 A1 | 7/2012 | Friedman et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0261575 A1 | 10/2013 | Kiyoshi |
| 2013/0267790 A1 | 10/2013 | Pfuetzner et al. |
| 2013/0303867 A1 | 11/2013 | Elfstrom et al. |
| 2013/0307570 A1 | 11/2013 | Bosaeus et al. |
| 2013/0324955 A1 | 12/2013 | Wong et al. |
| 2014/0051946 A1 | 2/2014 | Arne et al. |
| 2014/0133290 A1 | 5/2014 | Yokoo et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0303574 A1 | 10/2014 | Knutson |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0351690 A1 | 12/2015 | Toth et al. |
| 2015/0374896 A1 | 12/2015 | Du et al. |
| 2016/0015570 A1 | 1/2016 | Heinecke et al. |
| 2016/0084869 A1 | 3/2016 | Yuen et al. |
| 2016/0158056 A1 | 6/2016 | Davis et al. |
| 2016/0158969 A1 | 6/2016 | Mclane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Mrtensson et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079530 A1 | 3/2017 | Dimaio et al. |
| 2017/0079576 A1 | 3/2017 | Stroebech et al. |
| 2017/0112658 A1 | 4/2017 | Hosono |
| 2017/0156920 A1 | 6/2017 | Hunt et al. |
| 2017/0262986 A1 | 9/2017 | Xiong et al. |
| 2017/0319073 A1 | 11/2017 | Dimaio et al. |
| 2017/0340474 A1* | 11/2017 | Thirstrup ............... A61B 5/746 |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0367654 A1 | 12/2017 | Cheng et al. |
| 2018/0021164 A1 | 1/2018 | Fenton |
| 2018/0021165 A1 | 1/2018 | Fenton |
| 2018/0049667 A1 | 2/2018 | Heppe |
| 2018/0055359 A1 | 3/2018 | Shamim et al. |
| 2018/0078163 A1 | 3/2018 | Welch |
| 2018/0109852 A1 | 4/2018 | Mandapaka et al. |
| 2018/0171183 A1 | 6/2018 | Sakurai et al. |
| 2018/0177626 A1 | 6/2018 | Israelson |
| 2018/0250156 A1 | 9/2018 | Lam |
| 2018/0344533 A1 | 12/2018 | Rovaniemi |
| 2019/0099552 A1 | 4/2019 | Zhang et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Munoz Herencia |
| 2020/0297244 A1 | 9/2020 | Brownhill et al. |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |

(56) References Cited

U.S. PATENT DOCUMENTS

| | | |
|---|---|---|
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0386368 A1 | 12/2021 | Carlsson et al. |
| 2022/0000652 A1 | 1/2022 | Thirstrup et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0378602 A1 | 12/2022 | Hansen et al. |

FOREIGN PATENT DOCUMENTS

| | | |
|---|---|---|
| CN | 104902399 A | 9/2015 |
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| DE | 3437950 A1 | 4/1985 |
| DE | 3836590 A1 | 5/1990 |
| DE | 19900611 C1 | 7/2000 |
| DE | 69722993 T2 | 7/2004 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0800804 A1 | 10/1997 |
| EP | 1275357 A2 | 1/2003 |
| EP | 1188157 B1 | 12/2005 |
| EP | 2000083 A2 | 12/2008 |
| EP | 2108345 A1 | 10/2009 |
| EP | 2453851 A2 | 5/2012 |
| EP | 2489561 A2 | 8/2012 |
| EP | 2601915 A1 | 6/2013 |
| EP | 2654646 A2 | 10/2013 |
| EP | 2738960 A1 | 6/2014 |
| EP | 3064179 A1 | 9/2016 |
| EP | 3213727 A1 | 9/2017 |
| EP | 3226946 A1 | 10/2017 |
| GB | 2219679 A | 12/1989 |
| GB | 2225951 A | 6/1990 |
| GB | 2308306 A | 6/1997 |
| GB | 2343628 A | 5/2000 |
| GB | 2465742 A | 6/2010 |
| GB | 2486968 A | 7/2012 |
| GB | 2542093 A | 3/2017 |
| GB | 2561193 A | 10/2018 |
| JP | 04-074882 A | 3/1992 |
| JP | 06-152077 A | 5/1994 |
| JP | 09-010184 A | 1/1997 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2009-519751 A | 5/2009 |
| JP | 2014-033745 A | 2/2014 |
| JP | 2014-054368 A | 3/2014 |
| KR | 10-1056989 B1 | 8/2011 |
| KR | 10-2012-0003987 A | 1/2012 |
| KR | 20-0485138 Y1 | 12/2017 |
| NL | 1001019 C2 | 2/1997 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007/133555 A2 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011/007355 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A1 | 12/2011 |
| WO | 2012/076022 A2 | 6/2012 |
| WO | 2012/084987 A2 | 6/2012 |
| WO | 2013/013197 A1 | 1/2013 |
| WO | 2014/004207 A1 | 1/2014 |
| WO | 2014/086369 A1 | 6/2014 |
| WO | 2015/007284 A1 | 1/2015 |
| WO | 2015/014774 A1 | 2/2015 |

(56) References Cited

FOREIGN PATENT DOCUMENTS

| WO | 2015/084462 A1 | 6/2015 |
|----|----------------|--------|
| WO | 2015/094064 A1 | 6/2015 |
| WO | 2015/187366 A1 | 12/2015 |
| WO | 2016/132738 A1 | 8/2016 |
| WO | 2016/166731 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/120432 A1 | 6/2019 |
| WO | 2019/161859 A1 | 8/2019 |
| WO | 2019/161860 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

OTHER PUBLICATIONS

International Search Report and Written Opinion received for PCT Patent Application No. PCT/DK2019/050243, mailed on Nov. 25, 2019, 15 pages.

* cited by examiner

OSTOMY APPLIANCE HAVING AN ELECTRICAL CONNECTOR

The present disclosure relates to an ostomy system, devices thereof, method of manufacturing and method for monitoring an ostomy appliance. The ostomy appliance system comprises an ostomy appliance and a device, such as an ostomy monitor device. In particular, the present disclosure relates to leakage classification and/or detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
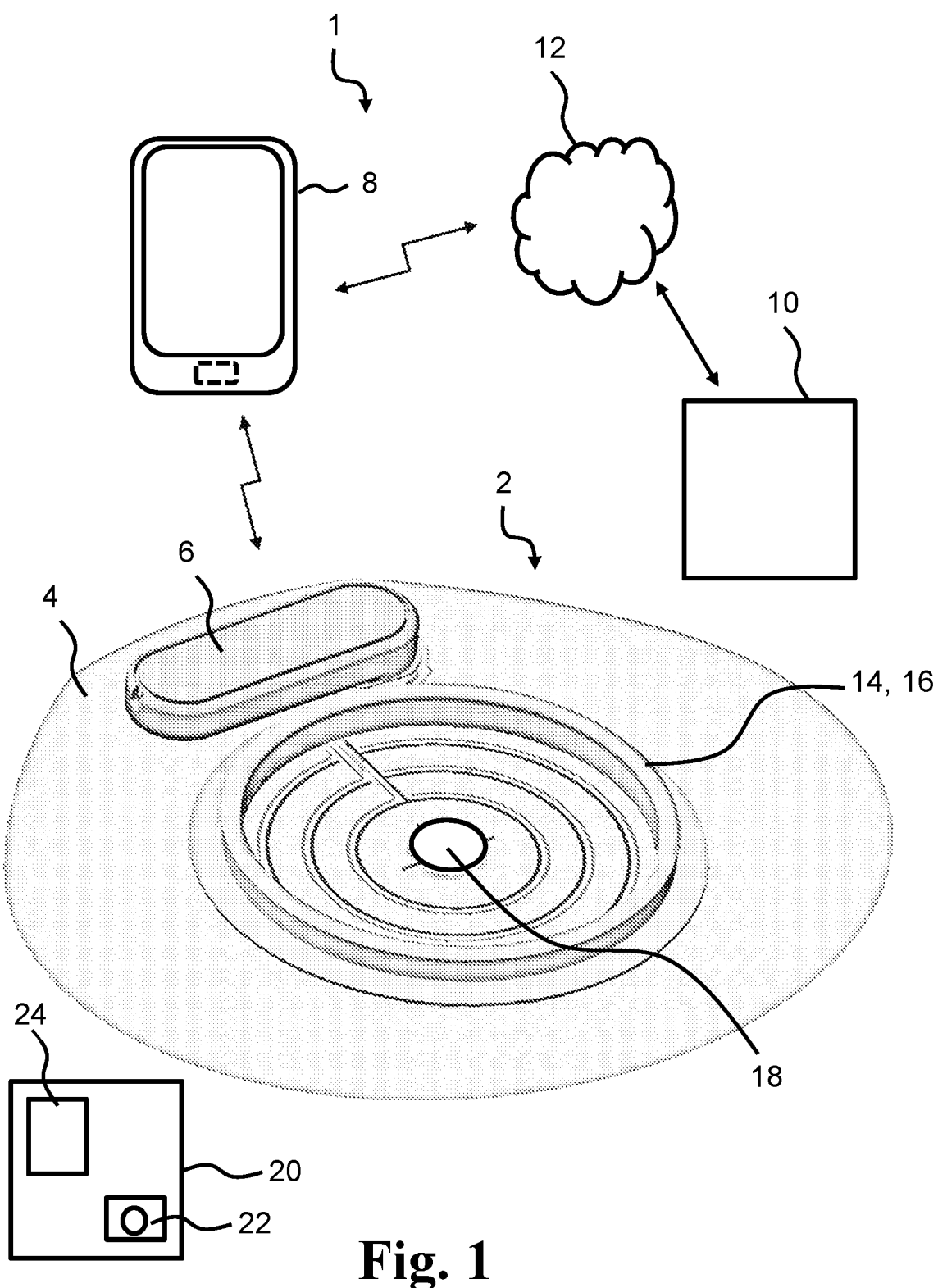
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part may comprise a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a center point.

The first adhesive layer may be made of a first composition. The first composition may comprise one or more polyisobutenes and/or styrene-isoprene-styrene. The first composition may comprise one or more hydrocoloids.

The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids.

The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be a second adhesive layer, also denoted rim adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocolloids.

The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is poly-isobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly/base plate may comprise a masking element configured to insulate at least parts of the electrodes from the first adhesive layer of the base plate and/or of the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm.

The base plate and/or the sensor assembly part may comprise a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part may be configured to electrically and/or mechanically couple the ostomy appliance and the monitor device.

The monitor interface of the base plate and/or of the sensor assembly part may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate and/or of the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or of the sensor assembly part, such as of the electrode assembly. The first intermediate element may be arranged between the terminal elements and the first adhesive layer. The first intermediate element may cover or overlap terminal element(s) of the base plate and/or of the sensor assembly part when seen in the axial direction. Thus, the first adhesive layer may be protected or experience more evenly distributed mechanical stress from the terminal elements of the base plate and/or of the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or of the sensor assembly part.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate and/or the sensor assembly part may have a stomal opening, e.g. with a center point. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates and/or sensor assembly parts, the user forms the stomal opening during preparation of the base plate for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or of the sensor assembly part, second ostomy data from a second electrode pair of the base plate and/or of the sensor assembly part, and third ostomy data from a third electrode pair of the base plate and/or of the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate and/or of the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate and/or of the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by
($P\_1\_1 < TH\_1\_1$),
($P\_2\_1 > TH\_1\_2$), and
($P\_3\_1 > TH\_1\_3$),
wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate. The first threshold values ($TH\_1\_1$, $TH\_1\_2$ and $TH\_1\_3$) may be the same or different, e.g. depending on the electrode configuration of the base plate. The first tertiary criterion ($P\_3\_1 < TH\_1\_3$) may be omitted in the first criteria set.

The first primary parameter $P\_1\_1$ may be indicative of the resistance between the first electrode pair (first electrode and first electrode part of the ground electrode) of the base plate.

The second primary parameter may be indicative of the resistance between the second electrode pair (second electrode and second electrode part of the ground electrode) of the base plate.

The third primary parameter may be indicative of resistance between the third electrode pair (third electrode and third electrode part of the ground electrode) of the base plate.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by
($P\_1\_1 < TH\_2\_1$),
($P\_2\_1 < TH\_2\_2$), and
($P\_3\_1 > TH\_2\_3$)
wherein $P\_1\_1$ is a first primary parameter based on the first parameter data and indicative of the resistance between the first electrode pair, $TH\_2\_1$ is a second primary threshold value, $P\_2\_1$ is a second primary parameter based on the second parameter data and indicative of the resistance between the second electrode pair, $TH\_2\_2$ is a second secondary threshold value, $P\_3\_1$ is a third primary parameter based on the third parameter data and indicative of the resistance between the third electrode pair, $TH\_2\_3$ is a second tertiary threshold value, and wherein the second operating state is indicative of medium degree of radial erosion on the base plate. The second threshold values ($TH\_2\_1$, $TH\_2\_2$ and $TH\_2\_3$) may be the same or different, e.g. depending on the electrode configuration of the base plate. The second primary criterion ($P\_1\_1 < TH\_2\_1$) and/or the second tertiary criterion ($P\_3\_1 > TH\_2\_3$) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by (P_1_1>TH_D_1), (P_2_1>TH_D_2), and (P_3_1>TH_D_3)

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate. The default threshold values (TH_D_1, TH_D_2 and TH_D_3) may be the same or different, e.g. depending on the electrode configuration of the base plate and/or of the sensor assembly part.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate and/or of the sensor assembly part has experienced a third degree of radial erosion, e.g. the first adhesive layer is eroded to the third radial distance of the third electrode pair.

The third criteria set may be given by (P_1_1<TH_3_1), (P_2_1<TH_3_2), and (P_3_1<TH_3_3)

wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate. The third threshold values (TH_3_1, TH_3_2 and TH_3_ 3) may be the same or different, e.g. depending on the electrode configuration of the base plate and/or of the sensor assembly part. The third primary criterion (P_1_1<TH_3_1) and/or the third secondary criterion (P_2_1<TH_3_2) may be omitted in the third criteria set.

In one or more exemplary monitor devices, the ostomy data comprises fourth ostomy data from a fourth electrode pair of the base plate and/or of the sensor assembly part. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by (P_4_1<TH_4_4)

wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part, e.g. a monitor coupling part, for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate and/or of a sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is a base plate, such as a base plate for an ostomy appliance, such as a base plate as disclosed above. Also, a sensor assembly part for a base plate of an ostomy appliance is disclosed, such as a sensor assembly part for being applied to a base plate.

The base plate defines a base plate plane. An axial direction is perpendicular to the base plate plane.

The base plate and/or the sensor assembly part may comprise a top layer, such as the top layer as disclosed above. The top layer may have a distal side and a proximal side. The distal side of the top layer may be exposed.

The base plate and/or the sensor assembly part may comprise an electrode assembly, such as the electrode assembly as disclosed above. The electrode assembly may have a distal side and a proximal side. The electrode assembly may comprise one or more electrodes including a first electrode and optionally a second electrode, a third electrode, a fourth electrode, a fifth electrode, a sixth electrode and/or a seventh electrode. The first electrode may comprise a first connection part. The first electrode may be provided, such as formed, on a proximal side of the electrode assembly. The electrode assembly may comprise a support layer. The first electrode may be provided, such as formed, on a proximal side of the support layer. The second electrode, the third electrode, the fourth electrode, the fifth electrode, the sixth electrode and/or the seventh electrode may comprise respective connection parts. The second electrode, the third electrode, the fourth electrode, the fifth electrode, the sixth electrode and/or the seventh electrode may be provided, such as formed, on the proximal side of the electrode assembly, such as on the proximal side of the support layer. A distal side of the electrode assembly may be facing the proximal side of the top layer.

The base plate and/or the sensor assembly part may comprise a monitor interface, such as the monitor interface as disclosed above. The monitor interface may be configured for connecting the base plate and/or the sensor assembly part to a device, such as a monitor device, an accessory device, a docking station or similar. The monitor interface may comprise a coupling part. The coupling part may comprise a proximal facing edge. The distal side of the electrode assembly may be facing the coupling part. The distal side of the top layer may be facing the coupling part. The coupling part may be bonded to the distal side of the top layer.

The monitor interface may comprise one or more terminal elements. The one or more terminal elements may include a first terminal element forming a first terminal of the base plate and/or the sensor assembly part. The one or more terminal elements may include a second terminal element forming a second terminal of the base plate and/or the sensor assembly part. The one or more terminal elements may include a third terminal element, a fourth terminal element, a fifth terminal element, a sixth terminal element and/or a seventh terminal element. The third terminal element, the fourth terminal element, the fifth terminal element, the sixth terminal element and/or the seventh terminal element may form respective terminals of the base plate and/or the sensor assembly part. A distal part of the first terminal element and/or the second terminal element and/or the third terminal element and/or the fourth terminal element and/or the fifth terminal element and/or the sixth terminal element and/or the seventh terminal element may be secured to the coupling part. A proximal part of the first terminal element may be in a position to contact the first connection part. A proximal part of the second terminal element and/or the third terminal element and/or the fourth terminal element and/or the fifth terminal element and/or the sixth terminal element and/or the seventh terminal element may be in a position to contact respective connection parts. The proximal part(s) may have lost contact to the respective connection part, e.g. if the material between the coupling part and the electrodes, e.g. due to viscous flow of material, has become thinner over time.

The monitor interface, such as the coupling part of the monitor interface, may be configured for connecting the base plate and/or the sensor assembly part to the device, such that, upon connection of the device to the base plate and/or the sensor assembly part, the connection part(s) of the one or more electrodes is forced towards the proximal part(s) of the one or more terminal elements, such as to reengage contact between the one or more terminal elements and respective electrodes.

A first axial distance measured between the proximal facing edge of the coupling part and a contact surface on a distal side of the top layer may be configured such that, upon connecting the sensor assembly part to a device, the device abuts the contact surface and displaces the first connection part into contact with the first terminal element.

The proximal facing edge of the coupling part may be configured for engagement with a distal facing edge of the device, e.g. in connecting the base plate and/or the sensor assembly part to the device.

An axial distance along the axial direction between the proximal facing edge of the coupling part and a contact surface on the distal side of the top layer may be a first axial distance. The contact surface may overlap the proximal part of the first terminal element and the first connection part. For example, the contact surface, the proximal part of the first terminal element and the first connection part may have at least one point in common in the base plate plane. The contact surface may be configured to abut a proximal facing side of the device, e.g. upon connecting the base plate and/or the sensor assembly part to the device.

The first axial distance may be less than a second axial distance. For example, the first axial distance may be between 0.01-1 mm less than the second axial distance, such as between 0.05-0.5 mm, such as between 0.1-0.3 mm. The second axial distance may be between the distal facing edge of the device and the proximal facing side of the device. For example, the first axial distance may be less than the second axial distance, such that upon connecting the base plate and/or the sensor assembly part to the device the proximal facing side of the device contacts the contact surface, e.g. to apply pressure on the contact surface, to force the first connection parts to contact the first terminal element.

Also disclosed is a device, such as a monitor device, such as a monitor device as disclosed above, an accessory device, a docking station or similar. The device may be configured for connecting to a base plate of an ostomy device or for connecting to a sensor assembly part for the base plate. The base plate defines a base plate plane and an axial direction being perpendicular to the base plate plane.

The device may comprise a device housing, such as a monitor device housing.

The device may comprise electronic circuitry. The electronic circuitry may include a processor and/or memory.

The device may comprise an appliance interface. The appliance interface may be configured for connecting the device to the base plate and/or the sensor assembly part. The appliance interface may comprise one or more terminals including a first terminal for forming electrical connection with a first terminal of the base plate and/or the sensor assembly part. The one or more terminals may include a second terminal, a third terminal, a fourth terminal, a fifth terminal, a sixth terminal and/or a seventh terminal for forming electrical connection with respective terminals of the base plate and/or the sensor assembly part. The appliance interface may comprise a device coupling part, such as a monitor coupling part as disclosed above. The device coupling part may comprise a distal facing edge. The distal facing edge may be configured for engagement with a proximal facing edge of the base plate and/or the sensor assembly part, e.g. in connecting the base plate and/or the sensor assembly part to the device.

The appliance interface, such as the device coupling part of the appliance interface, may be configured for connecting the device to the base plate and/or the sensor assembly part, such that, upon connection of the device to the base plate and/or the sensor assembly part, connection part(s) of the base plate and/or the sensor assembly part is forced towards proximal part(s) of one or more terminal elements, such as to reengage contact between the one or more terminal elements and respective connection parts.

An axial distance along the axial direction between the distal facing edge of the device coupling part and a proximal facing side of the device may be a second axial distance. The proximal facing side of the device may be configured to abut a contact surface of the base plate and/or the sensor assembly part, e.g. upon connecting the base plate and/or the sensor assembly part to the device.

The second axial distance may be more than a first axial distance. For example, the second axial distance may be between 0.01-1 mm more than the first axial distance, such as between 0.05-0.5 mm, such as between 0.1-0.3 mm. The first axial distance may be between the proximal facing edge of the base plate and/or the sensor assembly part and the contact surface of the base plate and/or the sensor assembly part. For example, the second axial distance may be more than the first axial distance, e.g. such that upon connecting the base plate and/or the sensor assembly part to the device the proximal facing side of the device contacts the contact surface of the base plate and/or the sensor assembly part, e.g. to apply pressure on the contact surface of the base plate and/or the sensor assembly part.

Also disclosed is a system, such as an ostomy system, such as an ostomy system as disclosed above. The ostomy system comprises a base plate, such as the base plate as disclosed above, and/or a sensor assembly part for the base plate, such as a sensor assembly part as disclosed above. The ostomy system comprises a device, such as a monitor device, an accessory device, a docking station or similar, configured to connect to the base plate and/or the sensor assembly part, such as the device as disclosed above. The base plate defines a base plate plane and an axial direction being perpendicular to the base plate plane.

The device may comprise a device housing, such as a monitor device housing.

The device may comprise electronic circuitry. The electronic circuitry may include a processor and/or memory.

The device may comprise an appliance interface. The appliance interface may comprise one or more terminals including a first terminal for forming electrical connection with a first terminal of the base plate and/or the sensor assembly part. The one or more terminals may include a second terminal, a third terminal, a fourth terminal, a fifth terminal, a sixth terminal and/or a seventh terminal for forming electrical connection with respective terminals of the base plate and/or the sensor assembly part. The appliance interface may comprise a device coupling part comprising a distal facing edge.

The base plate and/or the sensor assembly part may comprise a top layer, such as the top layer as disclosed above. The top layer may have a distal side and a proximal side. The distal side of the top layer may be exposed.

The base plate and/or the sensor assembly part may comprise an electrode assembly, such as the electrode assembly as disclosed above. The electrode assembly may have a distal side and a proximal side. The electrode assembly may comprise one or more electrodes including a first electrode and optionally a second electrode, a third electrode, a fourth electrode, a fifth electrode, a sixth electrode and/or a seventh electrode. The first electrode may comprise a first connection part. The first electrode may be provided, such as formed, on a proximal side of the electrode assembly. The electrode assembly may comprise a support layer. The first electrode may be provided, such as formed, on a proximal side of the support layer. The second electrode, the third electrode, the fourth electrode, the fifth electrode, the sixth electrode and/or the seventh electrode may comprise respective connection parts. The second electrode, the third electrode, the fourth electrode, the fifth electrode, the sixth electrode and/or the seventh electrode may be provided, such as formed, on the proximal side of the electrode assembly, such as on the proximal side of the support layer.

The base plate and/or the sensor assembly part may comprise a monitor interface, such as the monitor interface as disclosed above. The monitor interface may be configured for connecting the base plate and/or the sensor assembly part to the device. The monitor interface may comprise a coupling part. The coupling part may comprise a proximal facing edge. The distal side of the electrode assembly may be facing the coupling part. The distal side of the top layer may be facing the coupling part. The coupling part may be bonded to the distal side of the top layer.

The monitor interface may comprise one or more terminal elements. The one or more terminal elements may include a first terminal element forming a first terminal of the base plate and/or the sensor assembly part. The one or more terminal elements may include a second terminal element forming a second terminal of the base plate and/or the sensor assembly part. The one or more terminal elements may include a third terminal element, a fourth terminal element, a fifth terminal element, a sixth terminal element and/or a seventh terminal element. The third terminal element, the fourth terminal element, the fifth terminal element, the sixth terminal element and/or the seventh terminal element may form respective terminals of the base plate and/or the sensor assembly part. A distal part of the first terminal element and/or the second terminal element and/or the third terminal element and/or the fourth terminal element and/or the fifth terminal element and/or the sixth terminal element and/or the seventh terminal element may be secured to the coupling part. A proximal part of the first terminal element may be in a position to contact the first connection part. A proximal part of the second terminal element and/or the third terminal element and/or the fourth terminal element and/or the fifth terminal element and/or the sixth terminal element and/or the seventh terminal element may be in a position to contact respective connection parts. The proximal part(s) may have lost contact to the respective connection part, e.g. if the material between the coupling part and the electrodes, e.g. due to viscous flow of material, has become thinner over time.

The proximal facing edge of the base plate and/or the sensor assembly part may be configured for engagement with the distal facing edge of the device, e.g. in connecting the base plate and/or the sensor assembly part to the device.

An axial distance along the axial direction between the proximal facing edge of the coupling part and a contact surface on the distal side of the top layer may be a first axial distance. The contact surface may overlap the proximal part of the first terminal element and the first connection part. For example, the contact surface, the proximal part of the first terminal element and the first connection part may have at least one point in common in the base plate plane. The contact surface may be configured to abut a proximal facing side of the device, e.g. upon connecting the base plate and/or the sensor assembly part to the device.

An axial distance along the axial direction between the distal facing edge of the device coupling part and a proximal facing side of the device may be a second axial distance. The proximal facing side of the device may be configured to abut a contact surface of the base plate and/or the sensor assembly, e.g. upon connecting the base plate and/or the sensor assembly part to the device.

The first axial distance may be less than the second axial distance. For example, the first axial distance may be between 0.01-1 mm less than the second axial distance, such as between 0.05-0.5 mm, such as between 0.1-0.3 mm. The second axial distance may be between the distal facing edge of the device and the proximal facing side of the device. For example, the first axial distance may be less than the second axial distance, such that upon connecting the base plate and/or the sensor assembly part to the device the proximal facing side of the device contacts the contact surface, e.g. to apply pressure on the contact surface, to force the first connection parts to contact the first terminal element.

Because the proximal part(s) may have lost contact to the respective connection part(s), e.g. if the material between the coupling part and the electrodes, e.g. due to viscous flow of material, has become thinner over time, it may be necessary to provide for reengagement of the electrical connection between the proximal part(s) and the connection part(s). This may be achieved by dimensioning the device coupling part of the device and the coupling part of the monitor interface such that, upon connection of the device and the base plate and/or the sensor assembly part, pressure is applied to the contact parts, such that the contact parts and the proximal parts of the terminal elements are pressed together to provide for electrical connection between the two.

It may be noted that, the first axial distance and the second axial distance may be measured at cooperating positions configured to be aligned when the device and the base plate and/or the sensor assembly part is completely connected, i.e. when the device is in coupled position with respect to the base plate and/or the sensor assembly part. For example, in the case of the proximal facing edge of the coupling part and/or the distal facing edge of the device being inclined, the first axial distance may be measured from a first point of the proximal facing edge of the coupling part and the second axial distance may be measured from a second point of the distal facing edge of the device, wherein the first point and the second point are aligned and/or abutting when the device is completely connected to the base plate and/or the sensor assembly part.

The coupling part may be attached to the top layer. For example, the coupling part may be positioned on the distal side of the top layer and optionally the coupling part may be bonded, such as glued, soldered, or welded, to the top layer.

A contact surface of the base plate and/or the sensor assembly part may be configured to abut a proximal facing side of the device, e.g. upon connecting the base plate and/or the sensor assembly part to the device. The contact surface may be formed by the top layer. The contact surface may be a part of the top layer. The contact surface may be a part of the coupling part, e.g. the coupling part, such as a distal surface of the coupling part, may form the contact surface. For example, the coupling part may comprise a coupling flange. The coupling flange, such as a distal surface of the coupling flange may form the contact surface. The coupling flange may extend in the base plate plane. For example, the coupling flange may be parallel to the top layer. For example, the coupling flange may extend from a rim of the coupling part (explained in more detail below), such as radially extend from the rim of the coupling part. The coupling flange may be bonded to the top layer, such as glued, soldered, or welded, to the top layer.

The coupling part and/or the contact surface may be made of plastic. For example, the coupling part and/or the contact surface may be made of polyolefins, such as polyethylene, polypropylene, or similar. The coupling part and/or the contact surface may be made of polyethylene high-density. Alternatively or additionally, the coupling part and/or the contact surface may be made of acrylonitrile butadiene styrene. Alternatively or additionally, the coupling part and/or the contact surface may be made of polyphenylene oxide and/or polyethylene terephthalat and/or polybutylene terephthalate and/or polycarbonate and/or polyoxymethylene.

The contact surface may comprise a protrusion, e.g. extending in the axial direction. Alternatively or additionally, the proximal facing side of the device may comprise a protrusion, e.g. extending along the axial direction. The protrusion(s) may provide for a reduction of the contact area between the contact surface and the proximal facing side of the device when the base plate and/or the sensor assembly part and the device are connected. Thus, the protrusion(s) may provide for ease of connection, since the frictional force may be reduced. Alternatively or additionally, the protrusion(s) may be provided to establish the difference of distances between the first axial distance and the second axial distance.

The coupling part may comprise a rim. The rim may extend in the axial direction. The rim may comprise the proximal facing edge. For example, the rim may comprise a groove extending substantially parallel to the base plate plane. The groove may form the proximal facing edge. Alternatively or additionally, the rim may comprise a protrusion extending parallel to the base plate plane. The protrusion may form the proximal facing edge.

The base plate and/or the sensor assembly part may comprise a first adhesive layer, such as the first adhesive layer as disclosed above. The first adhesive layer may have a distal side facing the proximal side of the electrode assembly. The proximal part of the first terminal element, and optionally any other terminal element, may be located between the first adhesive layer and the electrode assembly.

The base plate and/or the sensor assembly part may comprise a second adhesive layer, such as the second adhesive layer as disclosed above. The second adhesive layer may have a distal side facing the proximal side of the top layer. The second adhesive layer may have a proximal side facing the distal side of the electrode assembly.

The base plate and/or the sensor assembly part may comprise one or more terminal elements. The one or more terminal elements may extend through the electrode assembly and the top layer and optionally the second adhesive layer. A distal part of each of the one or more terminal elements may extend into a terminal interface region, e.g. defined by the coupling part. The terminal interface region may be a region wherein terminals, e.g. of the base plate and/or sensor assembly part, may connect, such as mechanically and/or electrically connect, with respective terminals of a monitor device. A proximal part of each of the one or more terminal elements may contact respective connection parts of the one or more electrodes.

The terminal elements extending through the electrode assembly and optionally other layers may provide for a connection on the distal side of the base plate and/or the sensor assembly part allowing electrical connection to the one or more electrodes being provided on the proximal side of the electrode assembly.

The terminal elements may comprise one or more bends, such as a proximal terminal element bend and/or a distal terminal element bend. The proximal terminal element bend may provide that the proximal part of the terminal elements is in a position to contact respective connection parts. The distal terminal element bend may provide securing the distal part of the first terminal element to the coupling part, e.g. in that the distal part of each of the one or more terminal elements contact a surface, such as a distal surface, of the coupling part.

A terminal element bend, such as the proximal terminal element bend and/or the distal terminal element bend may form an angle, e.g. between 60-130 degrees, such as between 70-115 degrees, such as between 80-100 degrees. The angle of a terminal element bend, such as a proximal terminal element bend and/or a distal terminal element bend, may be defined relative to a straight terminal element, e.g. no bend has a 0 degrees angle and a U-shaped bend has a 180 degrees angle.

The device may comprise a proximal facing side. The proximal facing side of the device may be configured to abut a contact surface of the base plate and/or the sensor assembly part, e.g. upon connecting the base plate and/or the sensor assembly part to the device. The device housing, such as a proximal facing side of the device housing, may form the proximal facing side of the device.

The device coupling part may comprise a device rim. The device rim may extend along the axial direction. The device rim may comprise the distal facing edge. For example, the device rim may comprise a groove, e.g. extending substantially parallel to the base plate plane. The groove may form the distal facing edge. Alternatively or additionally, the device rim may comprise a protrusion, e.g. extending substantially parallel to the base plate plane. The protrusion may form the distal facing edge.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 is typically adjusted by the user or nurse before application of the ostomy appliance to accommodate the user's stoma.

Figure 2:
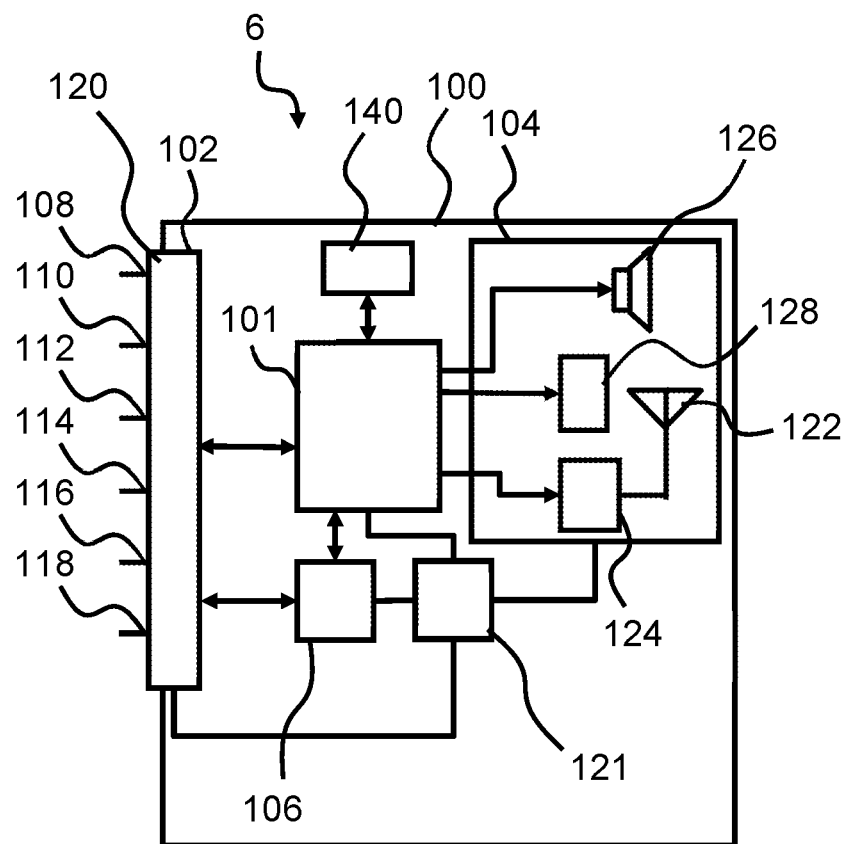
FIG. 2 illustrates an exemplary monitor device of the ostomy system.

The ostomy system 1 optionally comprises a docking station 20 forming an accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes, FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data.

The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

Figure 3:
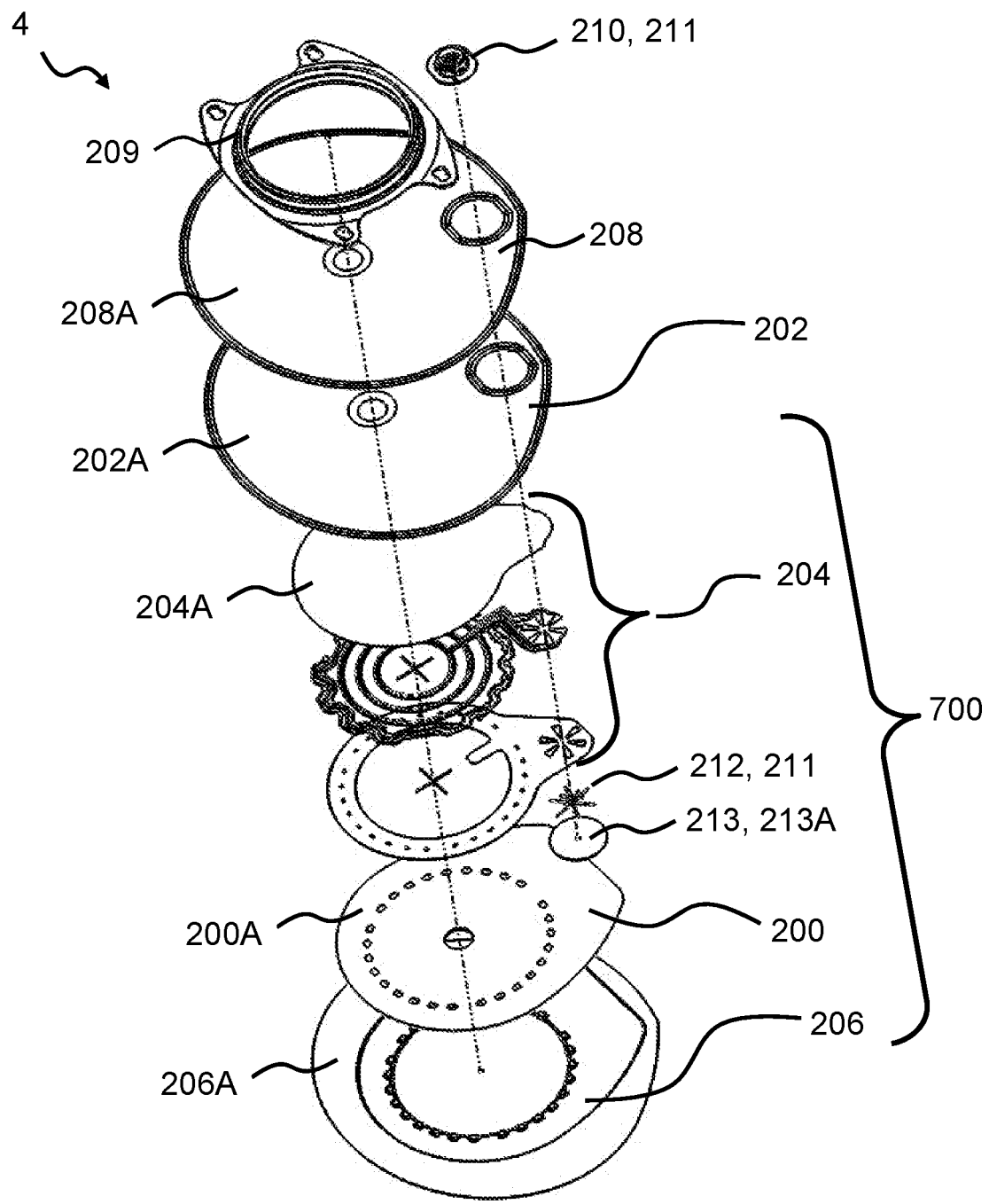
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
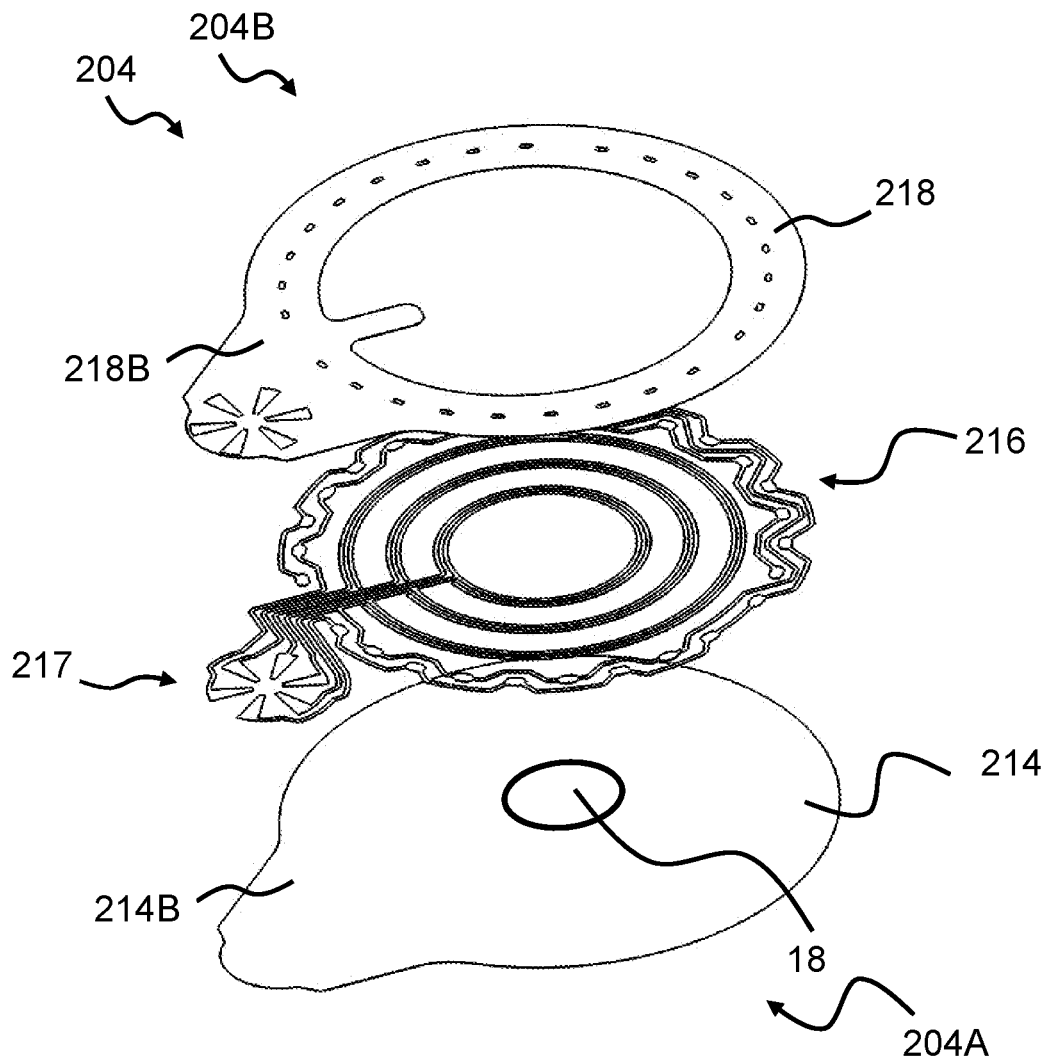
FIG. 4 is an exploded view of an exemplary electrode assembly.

FIG. 4 illustrates an exploded view of an exemplary electrode assembly 204 of a base plate and/or a sensor assembly part. The electrode assembly 204 has a distal side 204A and a proximal side 204B. The electrode assembly comprises a support layer 214 with proximal surface 214B and electrodes 216 including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are provided, such as formed, on a proximal side 214B of the support layer 214, e.g. the electrodes 216 may be positioned on the proximal side 214B of the support layer. Further, electrode assembly 204 comprises a masking element 218 with proximal surface 218B and configured to insulate electrode parts of electrodes 216 from the first adhesive layer of the base plate and/or the sensor assembly part. The masking element 218 covers or overlap with parts of the electrodes 216 when seen in the axial direction.

Figure 5:
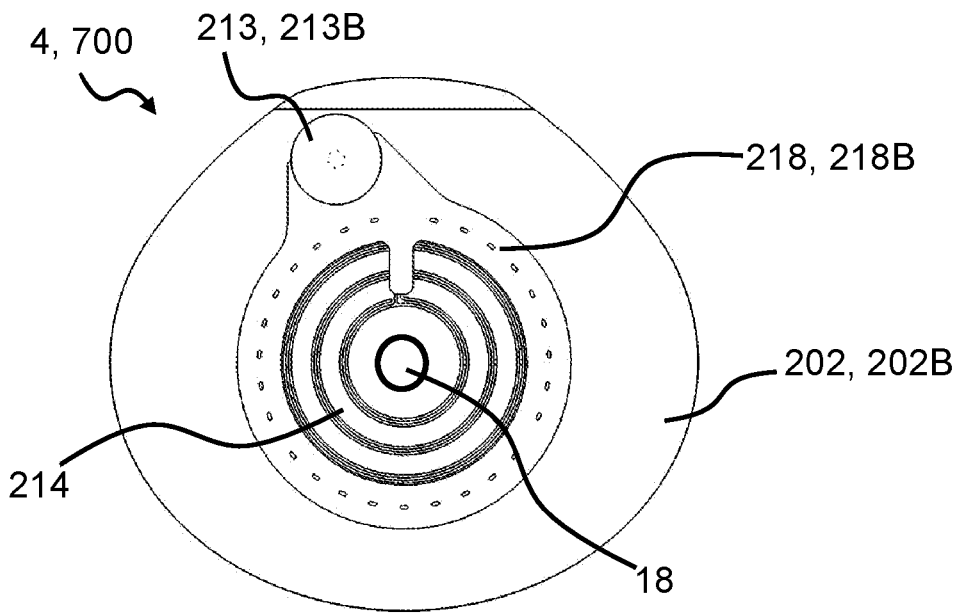
FIG. 5 is a proximal view of parts of a base plate and/or a sensor assembly part.

FIG. 5 is a proximal view of proximal surfaces of base plate parts of the base plate and/or a sensor assembly part without the first adhesive layer and the release liner. The base plate 4 and/or the sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or the sensor assembly part.

Figure 6:
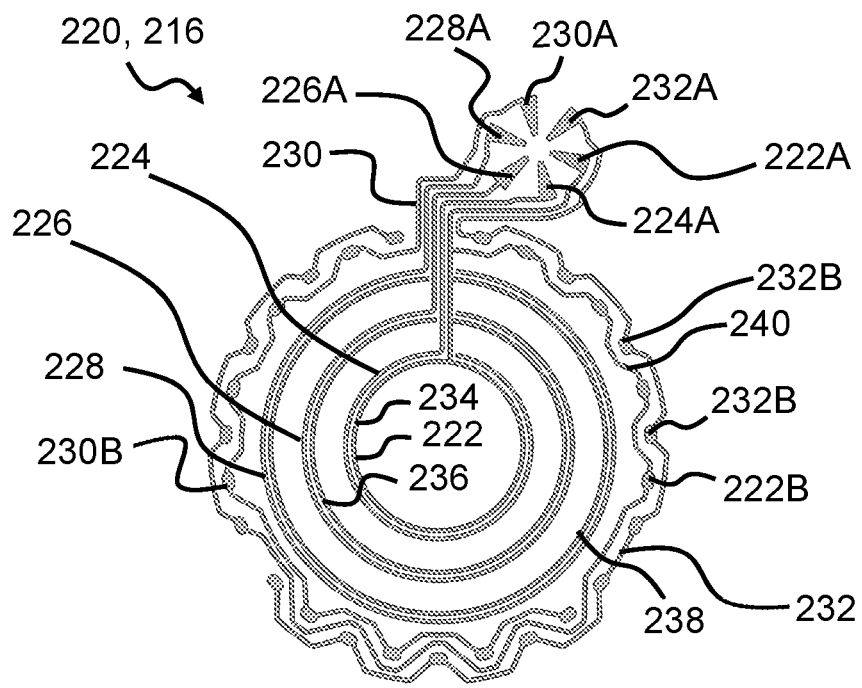
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

Figure 7:
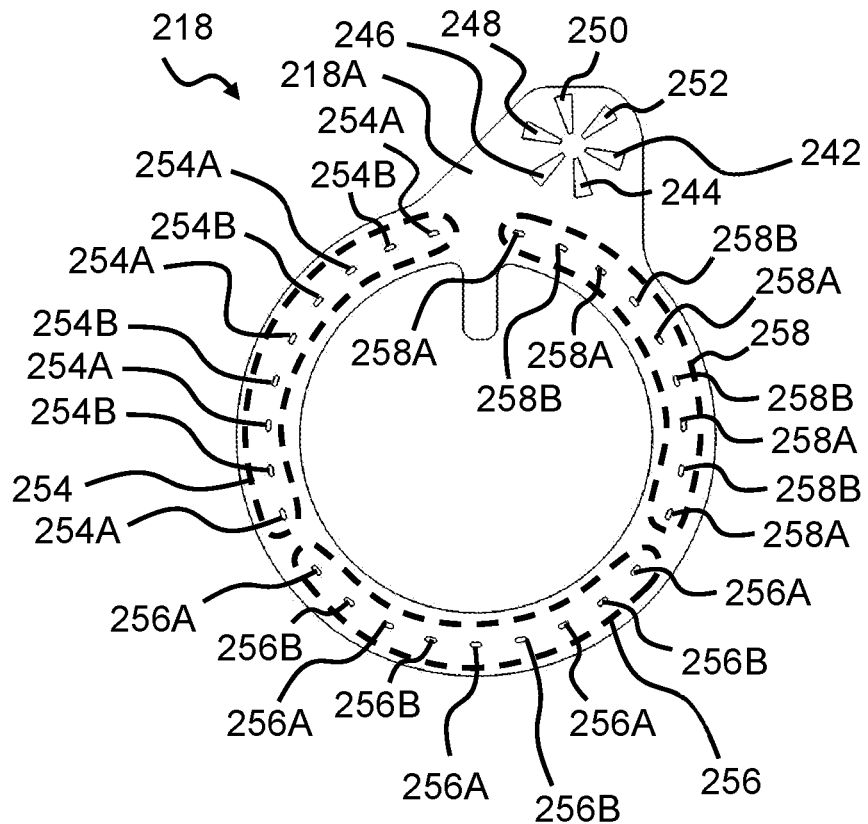
FIG. 7 is a distal view of an exemplary masking element.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
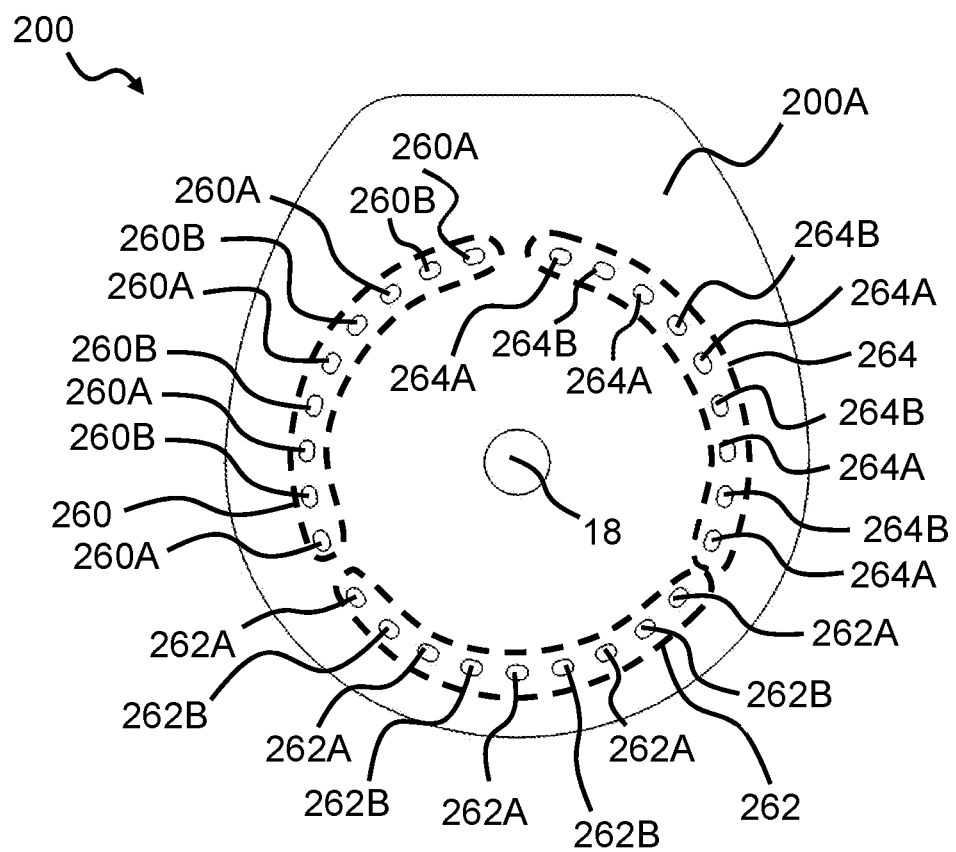
FIG. 8 is a distal view of an exemplary first adhesive layer.
Figure 9:
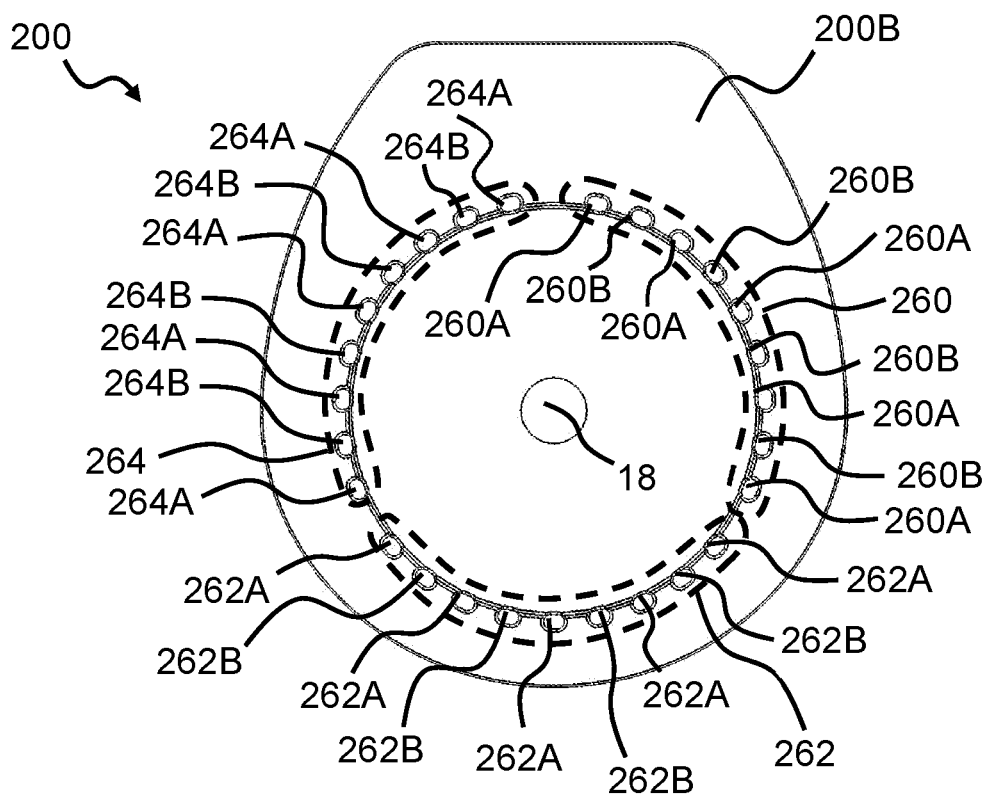
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
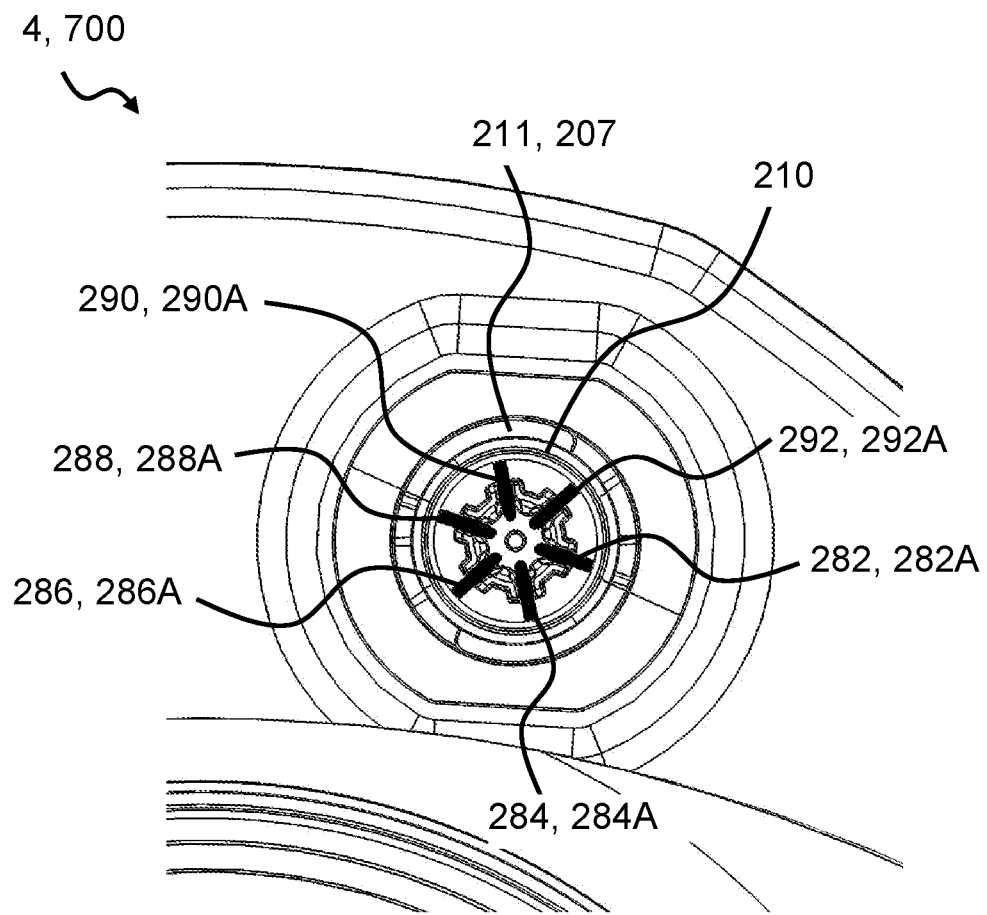
FIG. 10 is a distal view of a part of the base plate and/or sensor assembly part, FIG. 11 schematically illustrates a section of a base plate and/or a sensor assembly part, FIG. 12 schematically illustrates an exemplary monitor device, FIG. 13 schematically illustrates a cross sectional view of the monitor device, FIG. 14 schematically illustrates parts of an ostomy system.

FIG. 10 is a more detailed distal view of a part of the base plate 4 and/or the sensor assembly part 700. The base plate 4 and/or the sensor assembly part 700 comprises a monitor interface 207 of the base plate comprises the first connector 211. The first connector 211 comprises coupling part 210 configured to releasably couple the monitor device to the base plate and thus forming a releasable coupling. The first connector 211 and/or the monitor interface 207 comprises a plurality of terminals formed by respective terminal elements for forming respective electrical connections with respective terminals of the monitor device 207.

The plurality of terminals of the first connector 211 and/or monitor interface 207 comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

Figure 11:
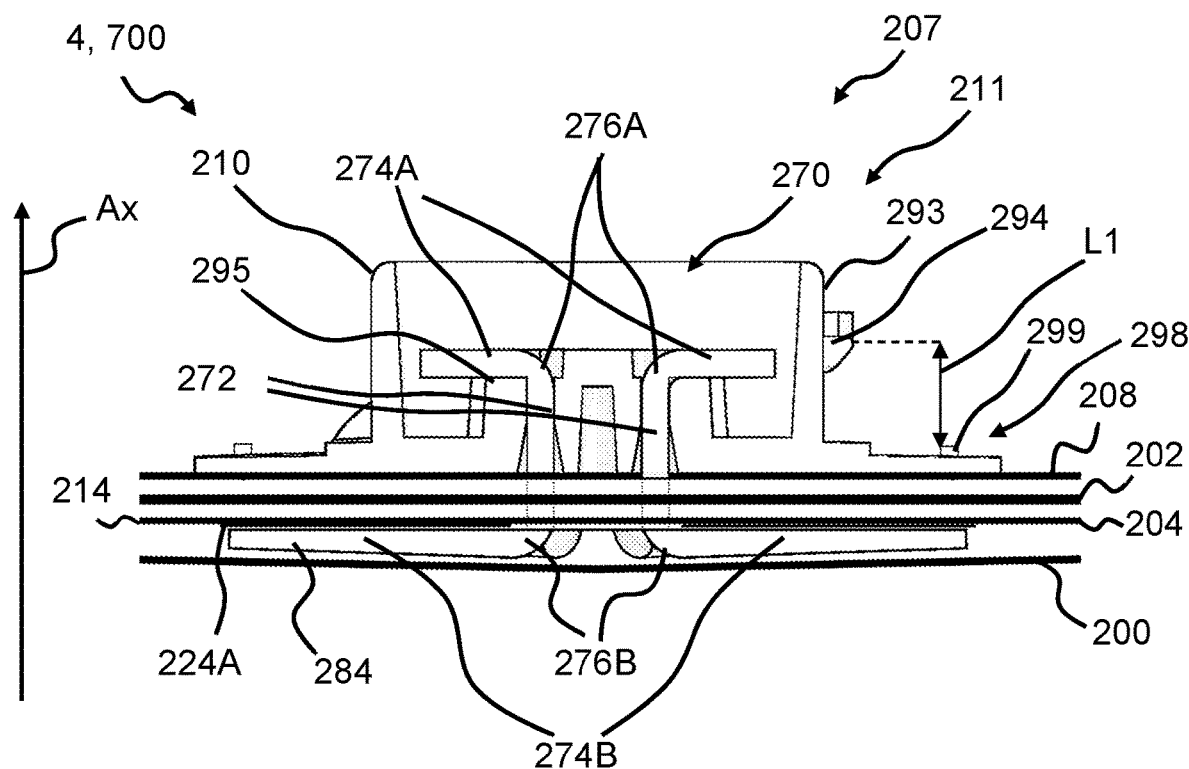

FIG. 11 schematically illustrates a section of a base plate 4 and/or a sensor assembly part 700 comprising a monitor interface 207. The monitor interface 207 comprises a first connector 211. The monitor interface 207 and/or the first connector 211 comprises a coupling part 210. The coupling part 210 defines a terminal interface region 270. The coupling part 210 comprises proximal facing edge 294.

The base plate 4 and/or the sensor assembly part 700 comprises an electrode assembly 204 having a distal side and a proximal side. The distal side of the electrode assembly 204 is facing the coupling part 210. The electrode assembly 204 comprises a plurality of electrodes including a first electrode. The first electrode comprises a first connection part 224A. The electrode assembly 204 may comprise a support layer 214, e.g. as disclosed in relation to previous figures. The electrodes are provided on a proximal side of the support layer 214. Alternatively, the electrodes may be provided on a distal side of the support layer 214.

The base plate 4 and/or the sensor assembly part 700 comprises a top layer 208. The top layer 208 has a distal side facing the coupling part 210 and a proximal side facing the distal side of the electrode assembly 204.

The base plate 4 and/or the sensor assembly part 700 comprises an optional second adhesive layer 202. The second adhesive layer 202 has a distal side facing the proximal side of the top layer 208. The second adhesive layer 202 has a proximal side facing the distal side of the electrode assembly 204.

The monitor interface 207 comprising a plurality of terminal elements 272 including a first terminal element 284. The first terminal element 284 forms a first terminal of the base plate 4 and/or the sensor assembly part 700, such as a first terminal of the monitor interface 207 of the base plate 4 and/or the sensor assembly part 700. A distal part 274A of the first terminal element 284 is secured to the coupling part 210. A proximal part 274B of the first terminal element 284 is in a position to contact the first connection part 224A. The proximal parts 274B may have lost contact to the respective connection parts, e.g. if the material between the coupling part and the electrodes, e.g. due to viscous flow of material, has become thinner over time.

The base plate 4 and/or the sensor assembly part 700 comprises a first adhesive layer 200. The first adhesive layer 200 has a distal side facing the proximal side of the electrode assembly 204. The proximal part 274B of the terminal elements 272, including the first terminal element 284, are located between the first adhesive layer 200 and the electrode assembly 204.

The terminal elements 272, including the first terminal element 284, extends through the electrode assembly 204, the second adhesive layer 202, and the top layer 208. Each of the terminal elements 272 have a distal part 274A extending into the terminal interface region 270 and a proximal part 274B extending to the proximal side of the electrode assembly 204. The terminal elements 272 comprises terminal element bends 276A; 276B between the proximal part 274B and the distal part 274A.

The distal part 274A of each of the terminal elements 272, e.g. including the first terminal element 284, contact a distal surface of the coupling part 210, e.g. in order to secure the terminal elements 272 to the coupling part 210.

The proximal facing edge 294 is configured for engagement with corresponding part of a device, such as a monitor device, an accessory device, a docking station or similar. For example, the proximal facing edge 294 is configured for engagement with a distal facing edge of the device, such as a monitor device (see FIG. 12-13) when the base plate 4 and/or the sensor assembly part 700 is connected to the device, such as fully connected with the device.

The coupling part 210 comprises a rim 293. The rim 293 extends in the axial direction Ax. The rim 293 comprises the proximal facing edge 294. For example, as shown in the illustrated example, the rim 293 comprises a protrusion extending substantially parallel to the base plate plane, and the lower part of the protrusion forms the proximal facing edge 294. In an alternative example, the rim 293 could have comprised a groove extending substantially parallel to the base plate plane, and the upper part of the groove could in such case form the proximal facing edge 294.

The base plate 4 and/or the sensor assembly part 700 comprises a contact surface 298, here shown as a coupling flange extending in the base plate plane from the rim 293. The contact surface 298 is on the distal side of the top layer. The contact surface 298 is configured to abut a side, such as a proximal facing side, of the device upon connecting the base plate 4 and/or the sensor assembly part 700 to the device. The contact surface is overlapping, e.g. in the base plate plane, the proximal part 274B of the terminal elements 272, such as the first terminal element 284, and the connection parts, such as the first connection part 224A. The contact surface 298, the proximal part 274B of the terminal elements 272 and the connection parts have at least one point in common in the base plate plane.

The contact surface 298 comprises an optional protrusion 299. The protrusion 299 extends in the axial direction Ax. The protrusion 299 may reduce the area of contact between the contact surface 298 and the device. Thus, the protrusion 299 may provide for ease of connection, e.g. in a rotational connection between the device and the base plate and/or the sensor assembly part, since the frictional force may be reduced.

An axial distance along the axial direction Ax between the proximal facing edge 294 of the coupling part 210 and the contact surface 298 is a first axial distance L1.

Figure 13:
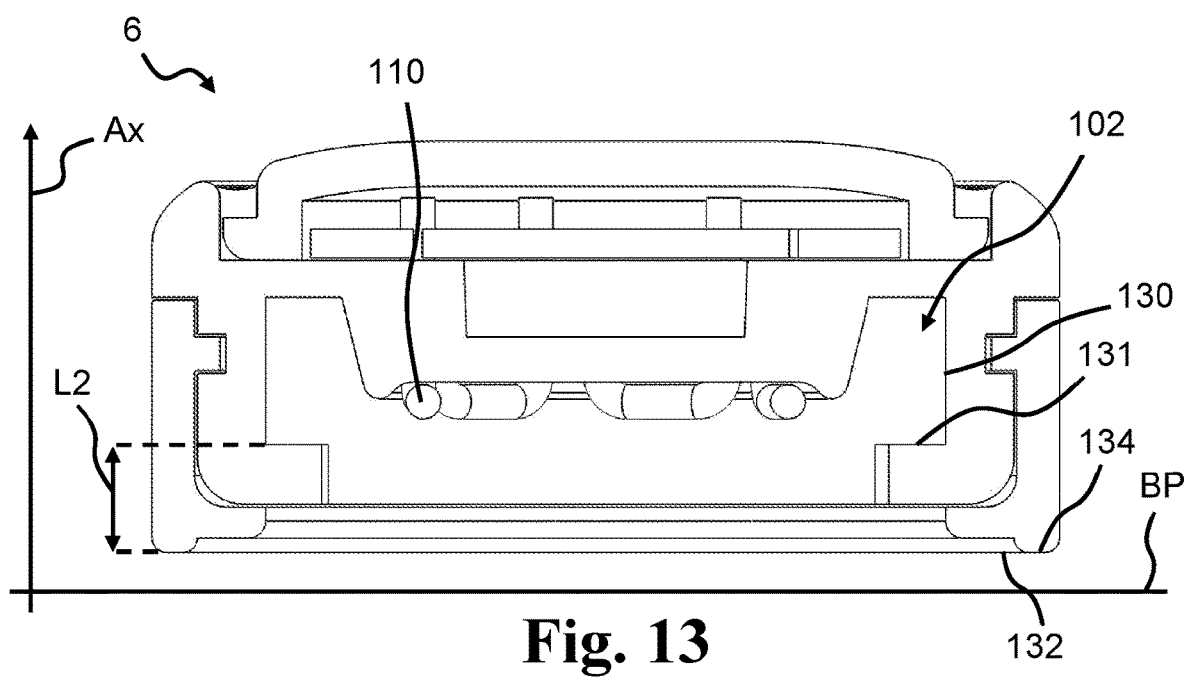

The first axial distance L1 is less than a corresponding distance of the device, such as a second axial distance (e.g. L2 of FIG. 13) between the distal facing edge of the device (e.g. 131 of FIG. 13) and the proximal facing side of the device (e.g. 132 of FIG. 13). The first axial distance L1 being smaller than the corresponding distance of the device provides that upon connecting the base plate 4 and/or the sensor assembly part 700 to the device the proximal facing side of the device contacts the contact surface 298 to force the first connection part 224A to contact the first terminal element 284. Thereby electrical connection between the first connection part and the first terminal element 284 may be re-established and/or reassured.

Figure 12:
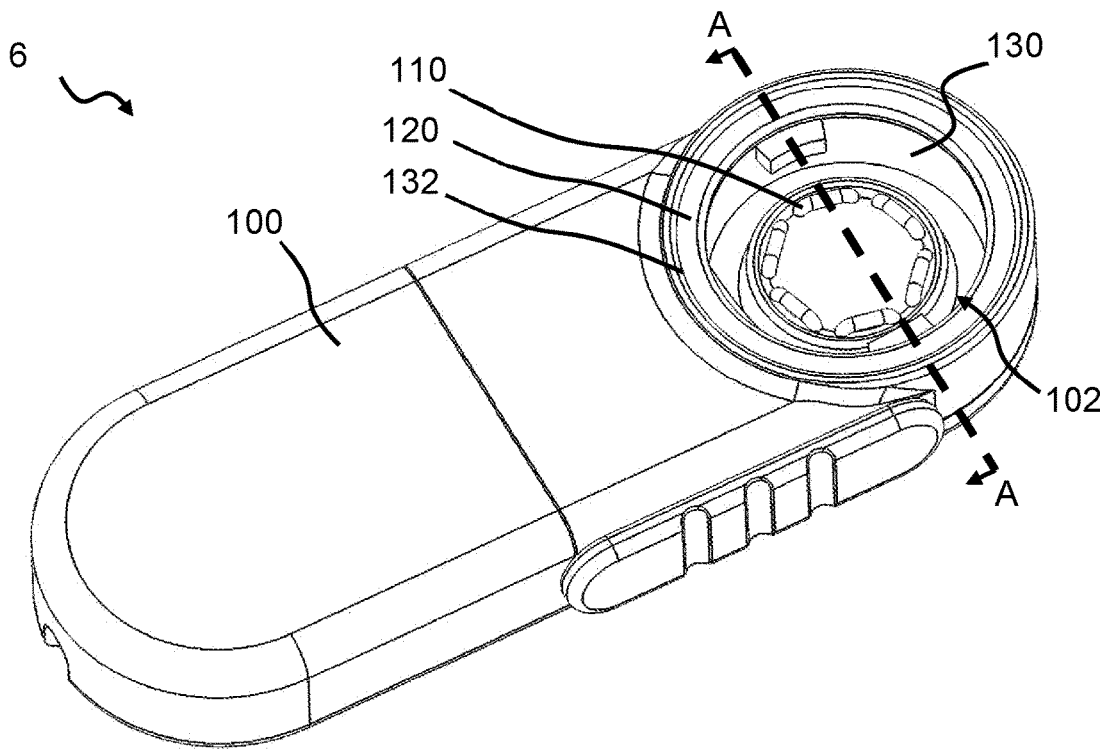

FIG. 12 schematically illustrates an exemplary monitor device 6, such as the monitor device as described in relation to previous figures. FIG. 12 is shown from the proximal side of the monitor device 6. FIG. 13 schematically illustrates a cross sectional view of the monitor device 6, as indicated by the line A-A.

The monitor device 6 is configured to connect to a base plate and/or a sensor assembly part of an ostomy device. The base plate defines a base plate plane BP and an axial direction Ax being perpendicular to the base plate plane BP. The base plate plane BP and the axial direction Ax are shown in FIG. 13, and corresponds to, if the monitor device 6 is connected to the base plate and/or the sensor assembly part as applied to the base plate.

The monitor device 6 comprises a monitor device housing 100.

The monitor device 6 comprises electronic circuitry, such as a processor.

The monitor device 6 comprises an appliance interface 102. The appliance interface 102 is configured for connecting the monitor device 6 to a base plate and/or the sensor assembly part, e.g. such as the base plate 4 and/or the sensor assembly part 700 as described in relation to FIG. 11. The appliance interface 102 comprises a plurality of terminals including a first terminal 110. The terminals are configured for forming electrical connections with respective terminals of the base plate and/or the sensor assembly part. For example, the first terminal is configured for forming an electrical connection with a first terminal of the base plate and/or the sensor assembly part. The appliance interface 102 comprises a monitor coupling part 120.

The monitor coupling part 120 comprises a distal facing edge 131. The distal facing edge 131 is configured for engagement with a corresponding part of the base plate and/or the sensor assembly part, such as a proximal facing edge of the base plate and/or the sensor assembly part (see FIG. 11) when the base plate and/or the sensor assembly part is connected to the monitor device 6.

The monitor coupling part 120 comprises a monitor rim 130. The monitor rim 130 extends along the axial direction Ax. The monitor rim 130 comprises the distal facing edge 131. For example, as shown in the illustrated example, the monitor rim 130 comprises a protrusion extending substantially parallel to the base plate plane, and the lower part of the protrusion forms the distal facing edge 131. In an alternative example, the monitor rim 130 could have comprised a groove extending substantially parallel to the base plate plane, and the upper part of the groove would form the distal facing edge 131.

The monitor device comprises a proximal facing side 132. The proximal facing side 132 may be formed by the monitor housing 100, as shown. The proximal facing side 132 is configured to abut a contact surface of the base plate and/or the sensor assembly part upon connecting the base plate and/or the sensor assembly part to the monitor device 6.

The proximal facing side 132 comprises an optional protrusion 134. The protrusion 134 extends along the axial direction. The protrusion 134 may reduce the area of contact between the proximal facing side 132 and the base plate and/or the sensor assembly part. Thus, the protrusion 134 may provide for ease of connection, e.g. in a rotational connection between the monitor device and the base plate and/or the sensor assembly part, since the frictional force may be reduced.

An axial distance along the axial direction Ax between the distal facing edge 131 of the monitor coupling part 120 and the proximal facing side 132 is a second axial distance L2.

The second axial distance L2 is more than a corresponding distance of the base plate and/or the sensor assembly part, such as a first axial distance (e.g. L1 of FIG. 11) between the proximal facing edge of the base plate (e.g. 294 of FIG. 11) and the contact surface of the base plate and/or the sensor assembly part (e.g. 298 of FIG. 11). The second axial distance L2 being more than the corresponding distance of the base plate and/or the sensor assembly part provides that upon connecting the base plate and/or the sensor assembly part to the monitor device 6 the proximal facing side of the monitor device contacts the contact surface of the base plate and/or the sensor assembly part. Thereby electrical connection between connection parts and terminal elements may be re-established and/or reassured.

Figure 14:
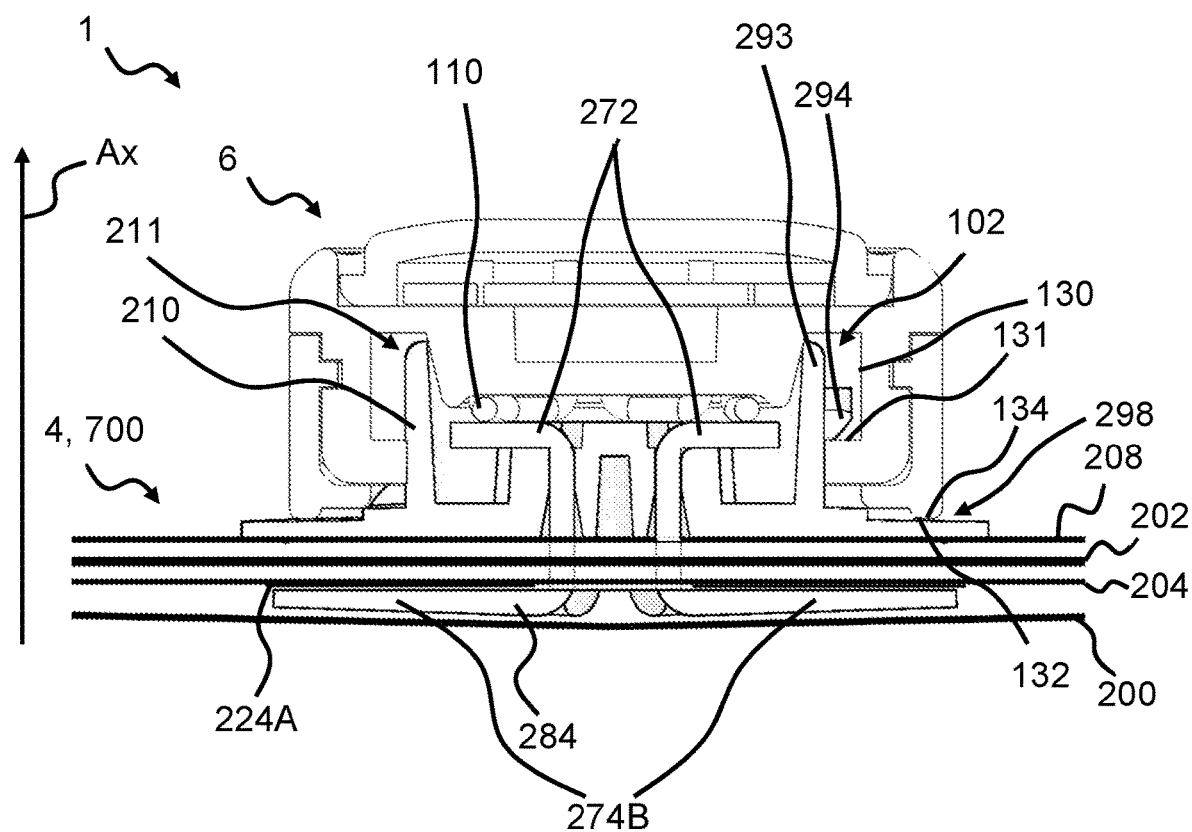

FIG. 14 schematically illustrates parts of an ostomy system 1, such as an ostomy system as described in relation to previous figures. The ostomy system 1 comprises a base plate 4 and/or a sensor assembly part 700, such as explained in relation to FIG. 11, and a monitor device 6, such as explained in relation to FIGS. 12 and 13. As seen in FIG. 14, the base plate 4 and/or the sensor assembly part 700 is connected to the monitor device 6.

The proximal facing edge 294 is engaging with the distal facing edge 131 of the monitor device 6.

Because the distance between the proximal facing edge 294 and the contact surface 298 of the base plate 4 and/or the sensor assembly part 700 is slightly less than the distance between the distal facing edge 131 and the proximal facing side 132 of the monitor device 6, pressure is provided on the contact surface 298 by the proximal facing side 132, and pressure is provided on the proximal facing edge 294 by the distal facing edge 131.

The proximal facing side 132 of the monitor device 6 is abutting the contact surface 298 of the base plate 4 and/or the sensor assembly part 700, and the contact surface 298, the top layer 208, the second adhesive layer 202, and the electrode assembly 204 is forced in the direction towards the proximal part 274B of the terminal elements 272. The terminal elements 272 are secured to the coupling part 210. Thus, the pressure provided on the proximal facing edge 294 forces the terminal elements 272 in the axial direction. Thereby, the proximal part 274B of the terminal elements 272 is forced to contact the connection parts of the electrode assembly, such as the first connection 224A. Thereby, electrical contact between the terminal elements 272 and their respective connection parts is ensured. The terminals of the monitor device 6 may therefore be electrically connected to the electrodes of the electrode assembly 204. For example, the first terminal 110 of the monitor device is electrically connected to a first electrode of the electrode assembly 204 via the first terminal element 284.

The position of the first connector on the base plate and/or the sensor assembly part, the number of terminals and the position of the terminals in the coupling part may be adapted to the electrode configuration used in the electrode assembly of the base plate and/or the sensor assembly part.

The use of the terms "first", "second", "third" and "fourth", "primary", "secondary", "tertiary" etc. does not imply any particular order, but are included to identify individual elements.

Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Embodiments of the present disclosure is set out in the following items:

1. Sensor assembly part for a base plate of an ostomy appliance, the base plate defining a base plate plane, an axial direction being perpendicular to the base plate plane, the sensor assembly part comprising:
    a top layer having a distal side and a proximal side;
    an electrode assembly comprising one or more electrodes including a first electrode, the first electrode comprising a first connection part, a distal side of the electrode assembly is facing the proximal side of the top layer;
    a monitor interface configured for connecting the sensor assembly part to a device, the monitor interface comprising a coupling part comprising a proximal facing edge, the distal side of the electrode assembly is facing the coupling part, and the monitor interface comprising one or more terminal elements including a first terminal element forming a first terminal of the sensor assembly part, a distal part of the first terminal element being secured to the coupling part and a proximal part of the first terminal element being in a position to contact the first connection part;
    wherein the proximal facing edge is configured for engagement with a distal facing edge of the device when the sensor assembly part is connected to the device,
    and wherein an axial distance along the axial direction between the proximal facing edge of the coupling part and a contact surface on the distal side of the top layer is a first axial distance, the contact surface overlapping the proximal part of the first terminal element and the first connection part, and the contact surface being configured to abut a proximal facing side of the device upon connecting the sensor assembly part to the device,
    the coupling part being configured such that the first axial distance is less than a second axial distance between the distal facing edge of the device and the proximal facing side of the device, such that upon connecting the sensor assembly part to the device the proximal facing side of the device contacts the contact surface to force the first connection part to contact the first terminal element.

2. Sensor assembly part according to item 1, wherein the coupling part comprises a coupling flange forming the contact surface, and wherein the coupling flange extends in the base plate plane.

3. Sensor assembly part according to any of the preceding items, wherein the contact surface is made of polyethylene high density.

4. Sensor assembly part according to any of the preceding items, wherein the contact surface comprises a protrusion extending in the axial direction.

5. Sensor assembly part according to any of the preceding items, wherein the coupling part comprises a rim extending in the axial direction, and wherein the rim comprises the proximal facing edge.

6. Sensor assembly part according to item 5, wherein the rim comprises a groove extending substantially parallel to the base plate plane, wherein the groove forms the proximal facing edge.

7. Sensor assembly part according to item 5, wherein the rim comprises a protrusion extending substantially parallel to the base plate plane, wherein the protrusion forms the proximal facing edge.

8. Sensor assembly part according to any of the preceding items comprising a first adhesive layer with a distal side facing the proximal side of the electrode assembly, and wherein the proximal part of the first terminal element is located between the first adhesive layer and the electrode assembly.

9. Sensor assembly part according to any of the preceding items comprising a second adhesive layer with a distal side facing the proximal side of the top layer and a proximal side facing the distal side of the electrode assembly.

10. A sensor assembly part for an ostomy appliance, the sensor assembly part comprising:
   a top layer;
   an electrode assembly comprising a first electrode having a first connection part, a distal side of the electrode assembly is facing a proximal side of the top layer;
   a coupling part attached to a first terminal element forming a first terminal of the sensor assembly part, a distal part of the first terminal element is secured to the coupling part and a proximal part of the first terminal element is spaced a distance from the first connection part;
   wherein a first axial distance measured between a proximal facing edge of the coupling part and a contact surface on a distal side of the top layer is configured such that, upon connecting the sensor assembly part to a device, the device contacts the contact surface and displaces the first connection part into contact with the first terminal element.

11. Base plate for an ostomy appliance, the base plate defining a base plate plane, an axial direction being perpendicular to the base plate plane, the base plate comprising:
   a top layer having a distal side and a proximal side;
   an electrode assembly comprising one or more electrodes including a first electrode, the first electrode comprising a first connection part, a distal side of the electrode assembly is facing the proximal side of the top layer;
   a monitor interface configured for connecting the base plate to a device, the monitor interface comprising a coupling part comprising a proximal facing edge, the distal side of the electrode assembly is facing the coupling part, and the monitor interface comprising one or more terminal elements including a first terminal element forming a first terminal of the base plate, a distal part of the first terminal element being secured to the coupling part and a proximal part of the first terminal element being in a position to contact the first connection part;
   wherein the proximal facing edge is configured for engagement with a distal facing edge of the device when the base plate is connected to the device,
   and wherein an axial distance along the axial direction between the proximal facing edge of the coupling part and a contact surface on the distal side of the top layer is a first axial distance, the contact surface overlapping the proximal part of the first terminal element and the first connection part, and the contact surface being configured to abut a proximal facing side of the device upon connecting the base plate to the device,
   the coupling part being configured such that the first axial distance is less than a second axial distance between the distal facing edge of the device and the proximal facing side of the device, such that upon connecting the base plate to the device the proximal facing side of the device contacts the contact surface to force the first connection part to contact the first terminal element.

12. Base plate according to item 11, wherein the coupling part comprises a coupling flange forming the contact surface, and wherein the coupling flange extends in the base plate plane.

13. Base plate according to any of items 11-12, wherein the contact surface is made of polyethylene high density.

14. Base plate according to any of items 11-13, wherein the contact surface comprises a protrusion extending in the axial direction.

15. Base plate according to any of items 11-14, wherein the coupling part comprises a rim extending in the axial direction, and wherein the rim comprises the proximal facing edge.

16. Base plate according to item 15, wherein the rim comprises a groove extending substantially parallel to the base plate plane, wherein the groove forms the proximal facing edge.

17. Base plate according to item 15, wherein the rim comprises a protrusion extending substantially parallel to the base plate plane, wherein the protrusion forms the proximal facing edge.

18. Base plate according to any of items 11-17 comprising a first adhesive layer with a distal side facing the proximal side of the electrode assembly, and wherein the proximal part of the first terminal element is located between the first adhesive layer and the electrode assembly.

19. Base plate according to any of items 11-18 comprising a second adhesive layer with a distal side facing the proximal side of the top layer and a proximal side facing the distal side of the electrode assembly.

20. A base plate for an ostomy appliance, the base plate comprising:
   a top layer;
   an electrode assembly comprising a first electrode having a first connection part, a distal side of the electrode assembly is facing a proximal side of the top layer;
   a coupling part attached to a first terminal element forming a first terminal of the sensor assembly part, a distal part of the first terminal element is secured to the coupling part and a proximal part of the first terminal element is spaced a distance from the first connection part;
   wherein a first axial distance measured between a proximal facing edge of the coupling part and a contact surface on a distal side of the top layer is configured such that, upon connecting the sensor assembly part to a device, the device contacts the contact surface and displaces the first connection part into contact with the first terminal element.

21. Device for connecting to a base plate of an ostomy appliance or for connecting to a sensor assembly part for the base plate, wherein the base plate defines a base plate plane and an axial direction being perpendicular to the base plate plane, the device comprising:
   a device housing;
   electronic circuitry;
   an appliance interface configured for connecting the device to the base plate or the sensor assembly, the appliance interface comprises one or more terminals including a first terminal for forming electrical connection with a first terminal of the base plate or the sensor assembly part, the appliance interface comprises a device coupling part comprising a distal facing edge;
   wherein the distal facing edge is configured for engagement with a proximal facing edge of the base plate or the sensor assembly part when the base plate or the sensor assembly part is connected to the device,
   and wherein an axial distance along the axial direction between the distal facing edge of the device coupling part and a proximal facing side of the device is a second axial distance, the proximal facing side of the device being configured to abut a contact surface of the base plate or the sensor assembly part upon connecting the base plate or the sensor assembly part to the device,
   the device coupling part being configured such that the second axial distance is more than a first axial distance between the proximal facing edge of the base plate or the sensor assembly part and the contact surface of the base plate or the sensor assembly part, such that upon connecting the base plate or sensor assembly part to the device the proximal facing side of the device contacts the contact surface of the base plate or the sensor assembly part.

22. Device according to item 21, wherein the electronic circuitry includes a processor.

23. Device according to any of items 21-22, wherein the device housing forms the proximal facing side of the device.

24. Device according to any of items 21-23, wherein the proximal facing side of the device comprises a protrusion extending along the axial direction.

25. Device according to any of items 21-24, wherein the device coupling part comprises a device rim extending along the axial direction, and wherein the device rim comprises the distal facing edge.

26. Device according to item 25, wherein the device rim comprises a groove extending substantially parallel to the base plate plane, wherein the groove forms the distal facing edge.

27. Device according to item 25, wherein the device rim comprises a protrusion extending substantially parallel to the base plate plane, wherein the protrusion forms the distal facing edge.

28. Device according to any of items 21-27, wherein the device is a monitor device configured to transmit monitor data to an accessory device, such as a phone.

29. Ostomy system comprising a base plate or a sensor assembly part for the base plate, and the ostomy system comprising a device configured to connect to the base plate or the sensor assembly part, the base plate defining a base plate plane and an axial direction being perpendicular to the base plate plane, the device comprising:
a device housing;
electronic circuitry;
an appliance interface, the appliance interface comprises one or more terminals including a first terminal for forming electrical connection with a first terminal of the base plate or the sensor assembly part, the appliance interface comprises a device coupling part comprising a distal facing edge;
the base plate or the sensor assembly part comprising:
a top layer having a distal side and a proximal side;
an electrode assembly comprising one or more electrodes including a first electrode, the first electrode comprising a first connection part, a distal side of the electrode assembly is facing the proximal side of the top layer;
a monitor interface, the monitor interface comprising a coupling part comprising a proximal facing edge, the distal side of the electrode assembly facing the coupling part, and the monitor interface comprising one or more terminal elements including a first terminal element forming the first terminal of the base plate or the sensor assembly part, a distal part of the first terminal element being secured to the coupling part and a proximal part of the first terminal element being in a position to contact the first connection part;
wherein the proximal facing edge of the base plate or the sensor assembly part is configured for engagement with the distal facing edge of the device when the base plate or the sensor assembly part is connected to the device,
and wherein an axial distance along the axial direction between the proximal facing edge of the coupling part and a contact surface on the distal side of the top layer is a first axial distance, the contact surface overlapping the proximal part of the first terminal element and the first connection part,
and wherein an axial distance along the axial direction between the distal facing edge of the device coupling part and the proximal facing side of the device is a second axial distance,
the first axial distance being less than the second axial distance, such that upon connecting the base plate or the sensor assembly part to the device the proximal facing side of the device contacts the contact surface to force the first connection parts to contact the first terminal element.

30. Ostomy system comprising a sensor assembly part according to any of items 1-10 or a base plate according to any of items 11-20, and the ostomy system comprising a device according to any of items 21-28.

LIST OF REFERENCES 1 ostomy system
2 ostomy appliance
4 base plate
6 monitor device
8 accessory device
10 server device
12 network
14 coupling member
16 coupling ring
18 stoma-receiving opening
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
122 antenna
124 wireless transceiver
126 loudspeaker
128 haptic feedback element
130 monitor rim
131 distal facing edge
132 proximal facing side
134 protrusion
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
207 monitor interface
208 top layer
208A distal surface of the top layer
208B proximal surface of the top layer
209 coupling ring
210 coupling part of first connector
211 first connector
212 terminals of first connector
213 first intermediate element 213A distal surface of first intermediate element
213B proximal surface of first intermediate element
214 support layer of electrode assembly
214A distal surface of support layer
214B proximal surface of support layer
217 connection parts of electrodes
216 electrodes of electrode assembly
218 masking element
218A distal surface of masking element
218B proximal surface of masking element
220 electrode configuration
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
270 terminal interface region
272 terminal element(s)
272A distal end of terminal element(s)
272B proximal end of terminal element(s)
274A distal part of terminal element(s)
274B proximal part of terminal element(s)
276A distal terminal element bend
276B proximal terminal element bend
278 guide hole
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
293 rim
294 proximal facing edge
295 distal surface
298 coupling flange
299 protrusion
700 sensor assembly part
M number of terminals in the first interface of the monitor device
L1 first axial distance
L2 second axial distance
BP Base plate plane
Ax Axial direction

The invention claimed is:

1. An ostomy appliance having an electrical connector, the ostomy appliance comprising:
an adhesive layer on a proximal side of the ostomy appliance, the adhesive layer adapted to secure the ostomy appliance to skin of a user;
a top layer on a distal side of the ostomy appliance;
an electrode assembly disposed between the adhesive layer and the top layer, with the electrode assembly comprising a first electrode;
a connector attached to the top layer, the connector adapted to provide electrical connection between a detachable data monitor and the electrode assembly, the connector comprising:
a coupling element projecting axially away from the top layer in a distal direction with a proximal facing edge projecting in a radial direction away from the coupling element, and
a first terminal element comprising a proximal part connected to the first electrode and a distal part connected to the coupling element;
wherein, when the detachable data monitor is mechanically coupled with the connector, the proximal facing edge of the coupling element presses the first terminal element axially to e electrical contact with the first electrode.

2. The ostomy appliance of claim 1, wherein the connector further comprises a protrusion formed distal to the top layer, with the protrusion adapted to mechanically coupled with the detachable data monitor.

3. The ostomy appliance of claim 1, wherein the coupling element provides a pocket sized to receive a portion of the detachable data monitor and the first terminal element is located within the pocket of the coupling element.

4. The ostomy appliance of claim 1, wherein the terminal element further comprises a central portion;
wherein the proximal part of the first terminal element is disposed between the adhesive layer and the top layer, the distal part of the first terminal element is distal to the top layer, and the central portion of the terminal element projects through the top layer.

5. The ostomy appliance of claim 1, wherein the electrode assembly comprises a plurality of electrodes including the first electrode and a second electrode and further comprises:
a second terminal element connected to and extending between the second electrode and the coupling element.

6. The ostomy appliance of claim 1, wherein the connector further comprises a coupling flange attached to the top layer of the ostomy appliance, wherein the coupling element is integrated with the coupling flange.

7. The ostomy appliance of claim 1, wherein the electrode assembly further comprises a support layer, with the electrode assembly disposed on a proximal side of the support layer.

8. The ostomy appliance of claim 1, further comprising an intermediate adhesive layer disposed between the electrode assembly and the top layer.

9. The ostomy appliance of claim 1, further comprising:
   a support layer disposed on a distal side of the electrode assembly; and
   an intermediate adhesive layer disposed between the support layer and the top layer;
   wherein the first terminal element connects between the first electrode and the coupling element of the connector.

10. The ostomy appliance of claim 1, wherein the electrode assembly and the connector combine to provide a sensor assembly adapted to sense and determine moisture propagation in the adhesive layer.

11. The ostomy appliance of claim 1, wherein the electrode assembly and the connector combine to provide a sensor assembly adapted to communicate data to the detachable data monitor related to a time for replacement of the ostomy appliance prior to stoma-output leakage relative to the adhesive layer.

\* \* \* \* \*